(12) United States Patent
Gilboa et al.

(10) Patent No.: US 6,702,780 B1
(45) Date of Patent: Mar. 9, 2004

(54) STEERING CONFIGURATION FOR CATHETER WITH RIGID DISTAL DEVICE

(75) Inventors: Pinhas Gilboa, Haifa (IL); David Tolkowsky, Tel Aviv (IL); Danny Blecher, Ramat Gan (IL)

(73) Assignee: Super Dimension Ltd., Herzelia (IL)

( * ) Notice: Subject to any disclaimer, the term of this patent is extended or adjusted under 35 U.S.C. 154(b) by 170 days.

(21) Appl. No.: 10/009,762

(22) PCT Filed: Sep. 7, 2000

(86) PCT No.: PCT/IL00/00537

§ 371 (c)(1),
(2), (4) Date: Mar. 5, 2000

(87) PCT Pub. No.: WO01/17579

PCT Pub. Date: Mar. 15, 2001

Related U.S. Application Data

(60) Provisional application No. 60/152,813, filed on Sep. 8, 1999.

(51) Int. Cl.[7] .............................................. A61M 37/00
(52) U.S. Cl. ..................... 604/95.04; 604/528; 600/434
(58) Field of Search .......................... 604/95.01–95.04, 604/96.01, 264, 523–524, 528–539; 600/372–374, 381, 393, 434, 435

(56) References Cited

U.S. PATENT DOCUMENTS 5,531,686 A 7/1996 Lundquist et al.
5,820,591 A * 10/1998 Thompson et al. ...... 604/95.01

FOREIGN PATENT DOCUMENTS

IL WO00/10456 3/2000

* cited by examiner

Primary Examiner—Brian L. Casler
Assistant Examiner—Michael M. Thompson
(74) Attorney, Agent, or Firm—Mark M. Friedman

(57) ABSTRACT

A steering configuration for facilitating steering of a catheter or the like provided with a rigid distal device employs a flexible support element to which a rigid device is attached at its distal end. At least one elongated flexible control element is configured such that tension applied to the control element causes flexing of the flexible support element. The control element is directly attached to the rigid device, thereby rendering the rigid device an operative extension of the steering mechanism.

4 Claims, 3 Drawing Sheets

STEERING CONFIGURATION FOR CATHETER WITH RIGID DISTAL DEVICE

This application claims the benefit of Provisional application Ser. No. 60/152,813, filed Sep. 8, 1999.

FIELD AND BACKGROUND OF THE INVENTION

The present invention relates to steerable catheters and, in particular, it concerns a steering configuration for facilitating steering of a catheter or the like provided with a rigid distal device.

Steerable catheters are well known in medical treatment of the heart. An example is a catheter for use in electrophysiology treatments, manufactured by EP Technologies, Inc., Sunnyvale, Calif., which is also described in U.S. Pat. No. 5,531,686 which is hereby incorporated by reference. FIGS. 2 and 3 of that patent, incorporated herein as FIGS. 2 and 3 of the present application, show the distal end steering portions 160 of a steering mechanism 10 of the catheter. A coiled spring or sleeve 170 defines a central lumen within a steering shaft 30, in which lumen a steering wire 120 is positioned. Protruding from ferrul 190, the distal end 150 of steering wire 120 is welded to a flat lead spring 230 at weld 260. When there is no tension on the steering wire, the lead spring tends to be kept unbent as shown in FIG. 2. While tension is placed on the steering wire 120 by manipulating a controller (not shown), the lead spring 230 and the distal end 150 of the steering wire are bent, thus turning the distal end 160 of the steering shaft 30.

It is often a desirable to couple a device at the distal end of such a catheter. An example is mounting a sensor device for measuring the location of the tip of the catheter, as described in PCT Publication No. WO0010456 which is hereby incorporated by reference. Such a device is formed as a solid cylinder, so that the leading spring and steering wire cannot extend through the device. As a result, such devices are typically attached as an extension to the end of the steering mechanism described, for example, by welding to the end of the catheter.

Addition of a rigid device to the end of a steerable catheter as described generates a significant degradation of the steerability of the catheter. Specifically, with reference to FIG. 4, it will be noted that the rigid device 1000 in such an arrangement always assumes a position corresponding to a straight non-steerable extrapolation of the direction in which the end portion 260 of lead spring 230 is directed. This interferes considerably with the maneuverability of the overall structure.

There is therefore a need for a steering configuration for facilitating steering of a catheter or the like provided with a rigid distal device which would enable the rigid device to be steered beyond the angle of the distal portion of the lead spring.

SUMMARY OF THE INVENTION

The present invention is a steering configuration for facilitating steering of a catheter or the like provided with a rigid distal device.

According to the teachings of the present invention there is provided, a steering configuration for facilitating steering of a catheter or the like provided with a rigid distal device, the steering configuration comprising: (a) a flexible support element having a proximal end and a distal end; (b) a rigid device attached to the distal end of the flexible support element; and (c) at least one elongated, flexible control element configured such that tension applied to the control element causes flexing of the flexible support element, wherein the control element is directly attached to the rigid device.

According to a further feature of the present invention, the rigid device is attached to the distal end of the flexible support at a first attachment region, and the control element is attached to the rigid device at a second attachment region, the second attachment region being removed from the first attachment region in such a manner that tension applied to the control element applies a turning moment between the rigid device and the flexible support in the first attachment region.

According to a further feature of the present invention, the flexible support is implemented as a spring element biased to return to a substantially straight position.

According to a further feature of the present invention, the flexible support is implemented as a leaf spring element.

According to a further feature of the present invention, the rigid device is a sensor.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a steering configuration for facilitating steering of a catheter or the like provided with a rigid distal device.

The principles and operation of steering configurations according to the present invention may be better understood with reference to the drawings and the accompanying description.

Figure 1A:
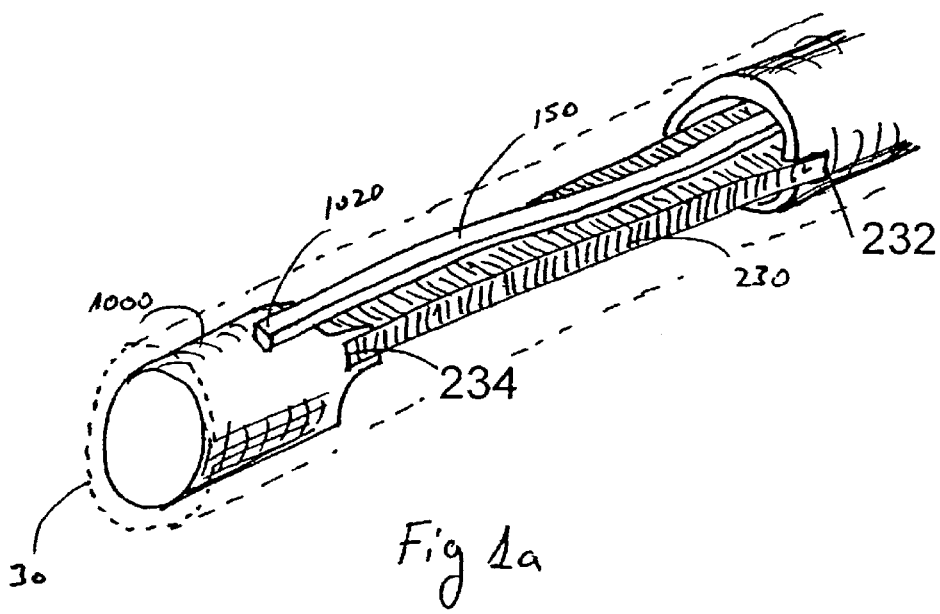
FIG. 1a is a schematic isometric view of a steering configuration, constructed and operative according to the teachings of the present invention, shown in a straight state.
Figure 1B:
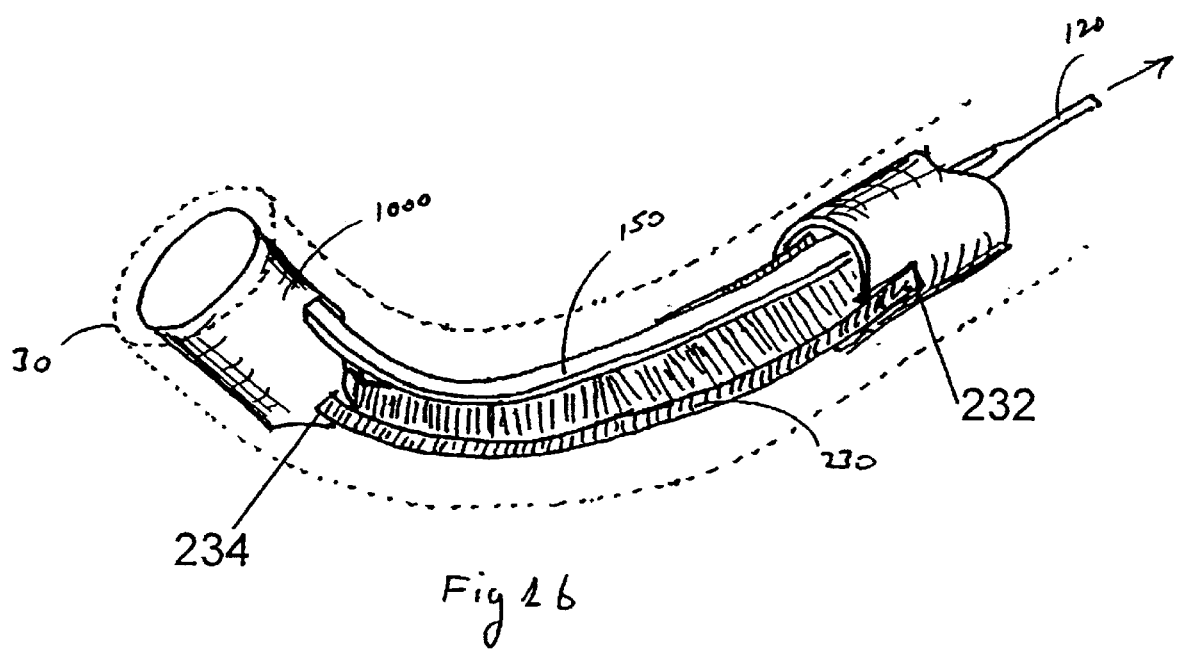
FIG. 1b is a schematic isometric view of the steering configuration of FIG. 1a in a deflected state.
Figure 2:
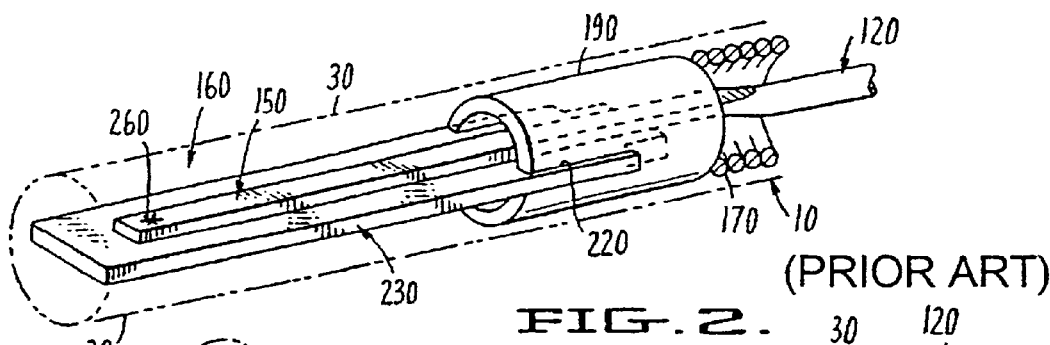
FIGS. 2 and 3 are representations of a prior art steering mechanism corresponding to FIGS. 2 and 3 of U.S. Pat. No. 5,531,686.
Figure 3:
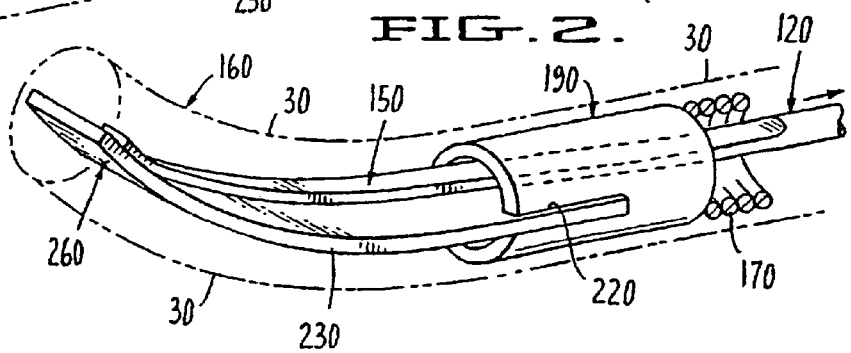
Figure 4:
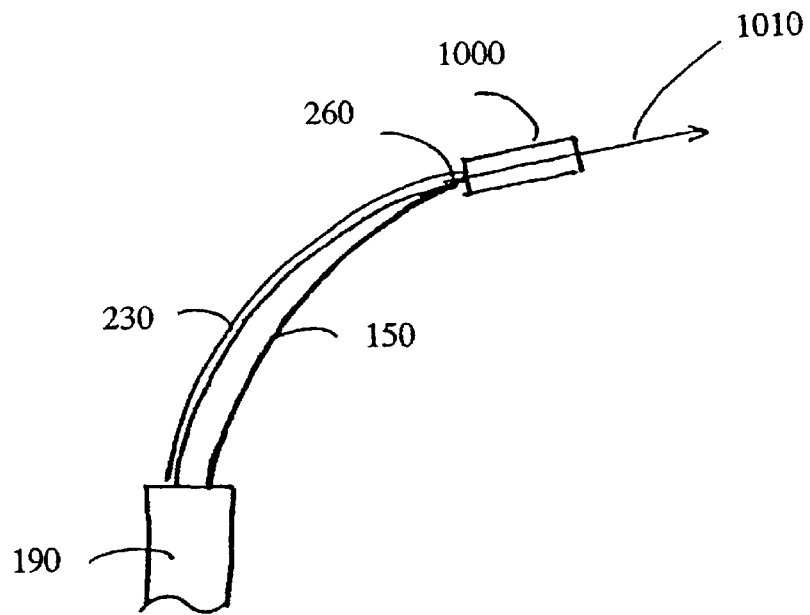
FIG. 4 is a schematic side view showing the direction assumed by a rigid device attached to the end of the steering mechanism of FIGS. 2 and 3.

Referring now to the drawings, FIGS. 1a and 1b show a steering configuration, constructed and operative according to the teachings of the present invention, for facilitating steering of a catheter or the like provided with a rigid distal device 1000.

Generally speaking, the steering configuration includes a flexible support element 230 having a proximal end 232 and a distal end 234. Rigid device 1000 is attached to distal end 234 of flexible support element 230. At least one elongated flexible control element 150 is configured such that tension applied thereto causes flexing of support element 230, thereby steering the catheter.

Figure 5:
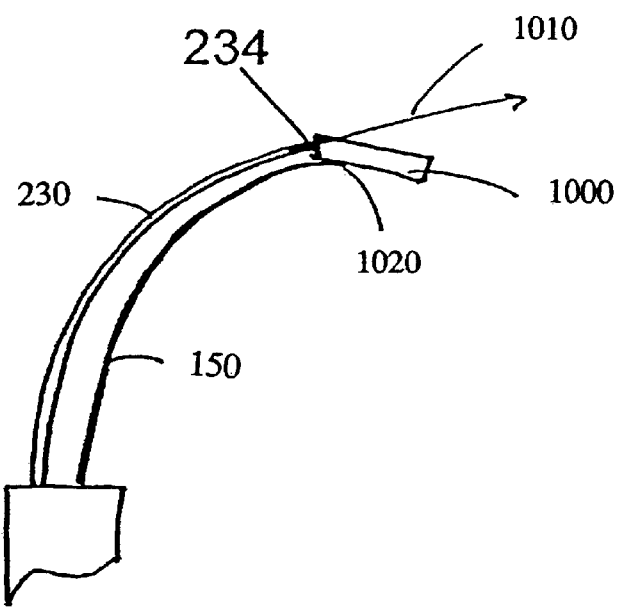
FIG. 5 is a schematic side view showing the direction assumed by the rigid device in the steering configuration of FIGS. 1a and 1b.

It is a particular feature of the steering configuration of the present invention that control element 150 is directly attached to rigid device 1000. This arrangement causes device 1000 to act as an operative extension of flexible support element 230. Specifically, when tension is applied via a steering wire 120 to control element 150, device 1000 is deflected as shown in FIGS. 1*b* and 5 such that a central axis of the device is deflected beyond the angle to which distal end 234 turns. FIG. 5 shows the additional deflection of device 1000 beyond the direction 1010 to which distal end 234 of support element 230 is deflected. This additional deflection greatly enhances the maneuverability of the steering configuration.

It will be appreciated that this configuration is suitable for coupling a wide range of devices onto steerable mechanisms in catheters and a range of other applications, medical and otherwise, where steerable mechanisms are used. By way of a non-limiting preferred example, the present invention is illustrated herein in the context of a sensor attached to the distal end of a steerable catheter.

Turning now to the features of the present invention in more detail, rigid device 1000 is typically attached to distal end 234 by welding, although a wide range of other forms of attachment or mechanical linkages may be used. Furthermore, in certain cases, device 1000 may be attached by being at least in part integrally formed together with support element 230.

Control element 150 is attached to device 1000 at an attachment region 1020. Here too, the attachment may be by welding, by production as an integral unit, or by any other suitable form of attachment or linkage. The position of attachment region 1020 is preferably chosen to be removed from the attachment region of end 234 with the device in such a manner that tension applied to control element 150 applies a turning moment between device 1000 and support element 230 in the attachment region of distal end 234. This enhances the additional deflection effect illustrated in FIG. 5.

It should be appreciated that the principles of the present invention may be used to modify a wide range of steering mechanisms for use with a distally mounted rigid device. Thus, by way of example, support element 230 may be a single flexible element or an articulated structure, and may be deployed as an axially extending internal element or as an outer sheath. In a most preferred implementation, support element 230 is implemented as a leaf spring element as shown, and is preferably biased to return to a substantially straight position.

It will be appreciated that the above descriptions are intended only to serve as examples, and that many other embodiments are possible within the scope of the present invention as limited only by the claims appended hereto.

What is claimed is:

1. A steering configuration for facilitating steering of a catheter or the like provided with a rigid distal device, the steering configuration comprising:

(a) a flexible support element having a proximal end and a distal end;

(b) a rigid device attached to said distal end of said flexible support element; and (c) at least one elongated flexible control element configured such that tension applied to said control element causes flexing of said flexible support element, wherein said control element is directly attached to said rigid device, and wherein said rigid device is a sensor.

2. The steering configuration of claim 1, wherein said rigid device is attached to said distal end of said flexible support at a first attachment region, and wherein said control element is attached to said rigid device at a second attachment region, said second attachment region being removed from said first attachment region in such a manner that tension applied to said control element applies a turning moment between said rigid device and said flexible support in said first attachment region.

3. The steering configuration of claim 1, wherein said flexible support is implemented as a spring element biased to return to a substantially straight position.

4. The steering configuration of claim 1, wherein said flexible support is implemented as a leaf spring element.

* * * * *